United States Patent
Rihan

(10) Patent No.: US 10,190,967 B1
(45) Date of Patent: Jan. 29, 2019

(54) FATIGUE CRACKING MACHINE FOR CIRCUMFERENTIAL NOTCHED TENSILE SPECIMENS

(71) Applicant: KUWAIT INSTITUTE FOR SCIENTIFIC RESEARCH, Safat (KW)

(72) Inventor: Rihan Omar Yousef Rihan, Safat (KW)

(73) Assignee: Kuwait Institute for Scientific Research, Safat (KW)

( * ) Notice: Subject to any disclaimer, the term of this patent is extended or adjusted under 35 U.S.C. 154(b) by 0 days.

(21) Appl. No.: 16/042,951

(22) Filed: Jul. 23, 2018

(51) Int. Cl.
G01N 19/08 (2006.01)
G01N 29/04 (2006.01)
G01N 17/00 (2006.01)
G01N 3/04 (2006.01)

(52) U.S. Cl.
CPC ............ *G01N 17/006* (2013.01); *G01N 3/04* (2013.01); *G01N 2203/0028* (2013.01); *G01N 2203/0064* (2013.01); *G01N 2203/0066* (2013.01); *G01N 2203/027* (2013.01); *G01N 2203/0208* (2013.01); *G01N 2203/0447* (2013.01)

(58) Field of Classification Search
CPC ............ G01N 3/04; G01N 2203/0028; G01N 2203/0208; G01N 2203/027; G01N 2203/006; G01N 2203/0062; G01N 2203/0064; G01N 2203/0066
USPC .......................................................... 73/799
See application file for complete search history.

(56) References Cited

U.S. PATENT DOCUMENTS

| 2,154,277 | A | * | 4/1939 | Moore | ..................... G01N 3/34 |
| | | | | | 73/812 |
| 2,243,413 | A | | 5/1941 | Buckingham | |
| 2,486,567 | A | | 11/1949 | Lazan | |

(Continued)

FOREIGN PATENT DOCUMENTS

| DE | 904479 C | * | 2/1954 | ............... G01N 3/34 |
| DE | 3204472 A1 | * | 8/1983 | ............... G01N 3/34 |
| JP | 58173451 A | | 10/1983 | |

OTHER PUBLICATIONS

English Translation of DE904479, Title: Feb. 18, 1954, Publisher: European Patent Office, pp. 4.*

(Continued)

*Primary Examiner* — Lisa Caputo
*Assistant Examiner* — Roger Hernandez-Prewit
(74) *Attorney, Agent, or Firm* — Richard C. Litman

(57) ABSTRACT

The fatigue cracking machine for circumferential notched tensile (CNT) specimens is a device for pre-cracking a CNT specimen prior to SCC testing. The machine uses a specimen holding cylinder attached to the shaft of a motor by a coupling, the holding cylinder being rotatably mounted in a bearing mounted in a bearing support fixed to a platform. The machine also uses a load cylinder rotatably mounted in a load bearing supported in a load fork, the load fork having a shaft adjustably mounted in a bearing support block. A dial indicator is fixed to a post rigidly mounted on the platform with the indicator's plunger bearing against the load bearing. An adjustment bolt bears against the end of the load fork shaft to displace the load bearing, applying a bending force to the specimen while it rotates, the displacement being measured by the dial indicator.

6 Claims, 7 Drawing Sheets

(56) References Cited

U.S. PATENT DOCUMENTS

| | | | | |
|---|---|---|---|---|
| 2,591,444 | A | * | 4/1952 | Lazan ..................... G01N 3/34 |
| | | | | 73/810 |
| 3,138,016 | A | | 6/1964 | Orner |
| 3,209,584 | A | * | 10/1965 | Lathrop .................. G01N 3/38 |
| | | | | 73/577 |
| 3,381,526 | A | | 5/1968 | Rastogi et al. |
| 3,680,367 | A | | 8/1972 | Krafft |
| 5,079,955 | A | | 1/1992 | Eberhardt |
| 8,474,324 | B2 | | 7/2013 | Rihan et al. |
| 9,541,485 | B1 | | 1/2017 | Rihan |

OTHER PUBLICATIONS

English Translation of Bibliographic Data and Abstract for DE3204472A1, Date: Aug. 18, 1983, Publisher: European Patent Office, pp. 2.*

Rihan et al., "The Determination of KISCC of Mild Steel in Hot Caustic by Using Small Circumferential Notched Tensile (CNT) Fracture Toughness Specimens", Structural Integrity and Fracture (2004), 8 sheets.

Raman et al., "Circumferential Nothch Tensile Testing Role of Imposed Electrochemical Potentials in Susceptibility of Steel to Caustic Cracking", J. Electrochem. Soc. (2007), vol. 154, Iss. 11, 2 pages (Abstract only).

Rihan et al., "Circumferential Notched Tensile Testing for Correlation of the Stress Intensity Factor (K I) and Stress Corrosion Crack Growth Rate", Metallurgical and Materials Transactions A (2008), vol. 39, Iss. 7, pp. 1475-1478.

Ikechukwu et al., "Design and Characterization of a Fatigue Testing Machine", Proceedings of the World Congress on Engineering and Computer Science (2013) vol. I, 7 pages.

Mathers, "Fatigue testing", 3 pages printed from www.twi-global.com/technical-knowledge/job-knowledge/fatigue-testing-078/ on Feb. 5, 2018.

* cited by examiner

FATIGUE CRACKING MACHINE FOR CIRCUMFERENTIAL NOTCHED TENSILE SPECIMENS

FIELD

The disclosure of the present patent application relates to material stress corrosion cracking testing, and particularly to a fatigue cracking machine for circumferential notched tensile specimens.

DESCRIPTION OF THE RELATED ART

In order to perform various tests, such as stress corrosion cracking (SCC), it is often necessary to utilize test specimens that have previously been fatigue cracked. One type of such test specimen is the circumferential notched tensile (CNT) specimen. In particular, the circumferential notch is machined into the circumference of the specimen. Fatigue pre-cracking before testing in a CNT testing device or an SCC testing device, such as those described in my prior patents, U.S. Pat. No. 8,474,324, issued to Rihan et al. Jul. 2, 2013, and U.S. Pat. No. 9,541,485, issued to Rihan Jan. 10, 2017, can be achieved by subjecting such CNT specimens to controlled simultaneous bending and rotation using a fatigue pre-cracking device. Initiation and subsequent propagation of the crack is monitored until a desired fatigue crack is achieved. The specimen may then be placed in a CNT or SCC testing device to test the ability of the specimen to withstand tensile stress and the point at which failure resulting from fatigue occurs under various conditions. Simultaneous rotation and bending of the CNT specimen often create difficulties when attempting to detect and monitor initiation and propagation of the fatigue pre-crack FIG. 4A illustrates a first conventional fatigue cracking device 500. The device includes a motor 510 having a first shaft 512 to transfer rotational output of the motor 510. A coupling 520 is used to connect the first shaft 512 to a first bearing housing 530. Specifically, the first bearing housing 530 includes a first bearing shaft 532 that is attached to the coupling 520 at one end. The first bearing housing 530 can also be attached to a mounting unit (not shown) via a pivot joint 542. The device 500 also includes a second bearing housing 540 which can be attached to a second mounting unit (not shown) using a pivot joint 534. As illustrated in FIG. 4A, a CNT specimen 550 is mounted on the device with one end disposed within the first bearing housing 530 and the other end disposed within the second bearing housing 540. A weight hanger 560 is configured such that one arm attaches to the first bearing housing 530 and a second arm attaches to the second bearing housing 540. A dead weight 562 is suspended from a bar extending between the two arms of the weight hanger 560. The pivot joints connected to the first bearing housing and the second bearing housing 540 allow a bending force to be generated on the CNT specimen 550 from the dead weight 562 attached to the weight hanger 560. A mechanical displacement indicator, specifically a dial indicator 570, is provided to measure the displacement of the second bearing housing 540 as a result of the initiation of the fatigue crack. While such a device is capable of generating a fatigue crack on the specimen 550, the problem with the device 500 is that it produces strong vibrations that cause the needle of the dial indicator 570 to oscillate to such an extent and over such a wide range that it is often difficult to obtain an accurate, consistent measurement of the displacement. Thus, operators are not able to accurately detect initiation and propagation of the crack through the CNT specimen 550.

FIG. 4B illustrates a second conventional fatigue pre-cracking device 600. The device 600 includes a motor 610 having a first shaft 612. A first coupling 614 is provided to connect the first shaft 614 to a second shaft 616. A second coupling 618 is used to connect the second shaft 616 to a first bearing housing 620 via a first bearing shaft 622. As illustrated in FIG. 4B, the first bearing housing 620 is connected to a first mount 624 by means of a pivot joint 626. A second bearing housing is provided along the same rotational axis as the first bearing housing 620. The second bearing housing 630 is connected to a second mount 632 by means of a second pivot joint 634. The motor 610, first mount 624, and second mount 632 are all positioned on common base 660. A CNT specimen 640 is mounted along the rotational axis with one end disposed in the first bearing housing 620, and the other end disposed within the second bearing housing 630. The CNT specimen 640 is aligned such that its circumferential notch 642 positioned is midway between the first bearing housing 620 and the second bearing housing 630.

A mounting bracket 650 is attached to both the first bearing housing 620 and the second bearing housing 630. An anchoring unit 652 is mounted on the base 660 at a preset distance from the mounting bracket 650. A loading bolt 654 is subsequently utilized to generate the bending force applied to the CNT specimen 640. More particularly, by threading the loading bolt 654 into the anchoring unit 652, the mounting bracket 650 is forced downward along with the first bearing housing 620 and the second bearing housing 630 in order to generate the bending force on the specimen 640. A load indicator, specifically a dial indicator 670, is subsequently utilized to measure the displacement resulting from the crack initiation. However, this device 600 is subject to the same problem as the device 500, i.e., the device 600 often vibrates to such a degree that the needle of the dial indicator 670 oscillates to such an extent that it is often difficult to obtain an accurate, consistent measurement of the displacement. The result, in either case, is that pre-cracking of the CNT specimen proceeds to such an extent that the CNT specimen fails prematurely during the fatigue cracking process.

FIG. 4C illustrates the cross-section of a typical CNT specimen 550 subjected to fatigue pre-cracking using the devices shown in FIGS. 4A and 4B. The CNT specimen 550 includes a circumferential notch 552, as seen in FIG. 4A, which has been machined on its surface. It can be seen that the fatigue cracked area 580 is uneven. This causes the ligament portion 590 (used for subsequent stress tests) to be located off-center. The specific shape of the ligament portion 590 may also be uneven.

Thus, a fatigue cracking machine for circumferential notched tensile specimens solving the aforementioned problems is desired.

SUMMARY

The fatigue cracking machine for circumferential notched tensile (CNT) specimens is a device for pre-cracking a CNT specimen prior to SCC testing. The machine uses a specimen holding cylinder attached to the shaft of a motor by a coupling, the holding cylinder being rotatably mounted in a bearing mounted in a bearing support fixed to a platform. The machine also uses a load cylinder rotatably mounted in a load bearing supported in a load fork, the load fork having a shaft adjustably mounted in a support block. A dial indicator is fixed to a post rigidly mounted on the platform with the indicator's plunger bearing against the load bearing. An adjustment bolt bears against the end of the load fork shaft to displace the load bearing, applying a bending force to the specimen while it rotates, the displacement being measured by the dial indicator.

The specimen is retained in the holding cylinder and in the loading cylinder by clamping bolts. Prior to rotating the motor shaft, the position of the CNT specimen is adjusted so that the notch in the specimen is aligned with the inlet of the blind bore in the holding cylinder so that the bending force applied by displacement of the load bearing is applied at the notch, which is where the pre-crack is formed in the specimen. Since the dial indicator is secured to a post independently mounted to the platform and since the load bearing is supported between the tines of the load fork, and since the shaft of the load fork is securely held by another clamp bolt, vibrations from rotation of the motor shaft are greatly reduced. This reduces oscillation of the dial indicator plunger, and eliminates wide swings of the indicator needle when the bending force is adjusted and during initiation and propagation of the crack, providing more accurate and constant measurements of the displacement of the load bearing, resulting in greater control of the pre-crack formed in the CNT specimen. It also permits termination of the cracking process before the crack has propagated far enough to result in premature failure during the pre-cracking process of the CNT specimen.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The fatigue cracking machine for circumferential notched tensile (CNT) specimens is a device for pre-cracking a CNT specimen prior to SCC testing. The machine uses a specimen holding cylinder attached to the shaft of a motor by a coupling, the holding cylinder being rotatably mounted in a bearing mounted in a bearing support fixed to a platform. The machine also uses a load cylinder rotatably mounted in a load bearing supported in a load fork, the load fork having a shaft adjustably mounted in a bearing support block. A dial indicator is fixed to a post rigidly mounted on the platform with the indicator's plunger bearing against the load bearing. An adjustment bolt bears against the end of the load fork shaft to displace the load bearing, applying a bending force to the specimen while it rotates, the displacement being measured by the dial indicator.

Figure 3A:
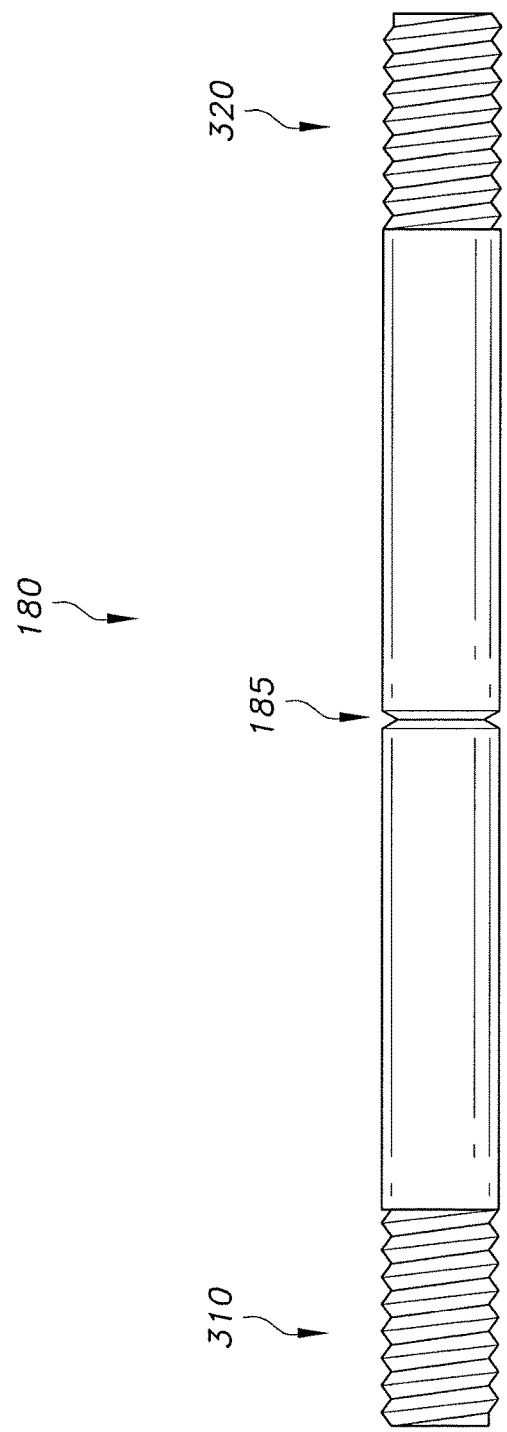
FIG. 3A is a side elevational view of a circumferential notched tensile (CNT) specimen.

As shown in FIG. 3A, a CNT specimen 180 is typically an elongated cylindrical shaft having a circumferential or annular notch 185 defined therein, usually about halfway along the length of the shaft. The opposing ends of the specimen may have external threads 310, 320 for securing the specimen in a testing device.

Figure 1:
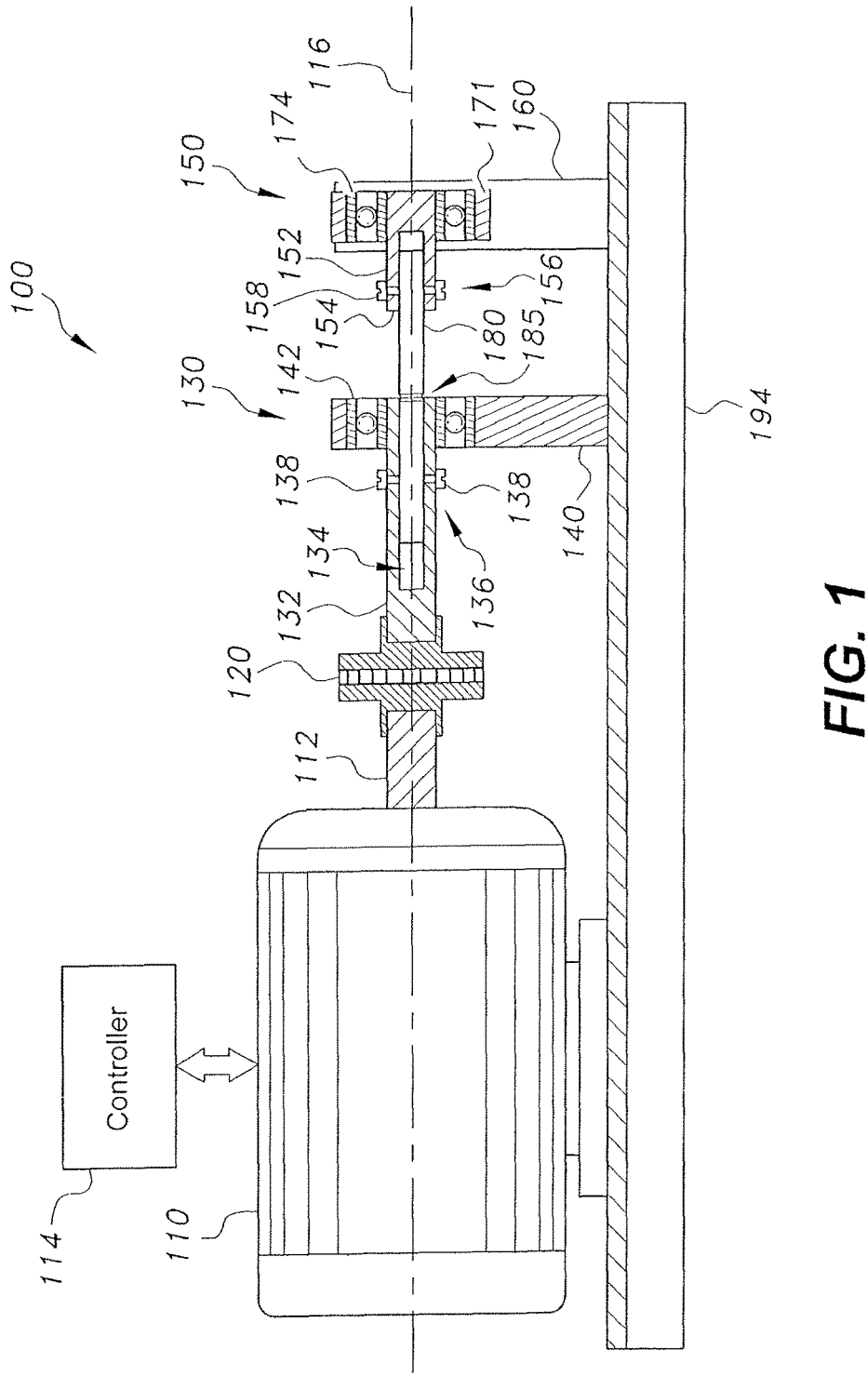
FIG. 1 is an environmental side view, partially in section, of a fatigue cracking machine for circumferential notched tensile (CNT) specimens.

As shown in FIG. 1, the fatigue cracking machine 100 includes a motor 110 securely mounted to a platform 194 or other supporting surface, a coupler 120, a rotating unit 130, and a loading unit 150. The motor 110 includes a motor shaft 112, which transmits the rotational motion generated by the motor 110. A controller 114 may be provided to control operation of the motor 110. For example, the controller 114 can be used to vary the rotational speed of the motor 110 so that specific rotational profiles (e.g., fixed, variable, intermittent, etc.) can be achieved.

The coupler 120 is used to connect the motor shaft 112 to the rotating unit 130. Depending on the specific implementation, the coupler 120 can be configured as a static coupler, which locks the motor shaft 112 and elements of the rotating unit 130 in place in order to achieve synchronous rotation about a rotational axis 116. Thus, the motor shaft 112 and elements of the rotating unit 130 would rotate at the same speed. However, the coupler 120 may alternatively be a viscous type coupler, which allows a limited amount of slip between the motor shaft 112 and elements of the rotating unit 130 based, for example, on the torque applied at the motor shaft 112.

Still referring to FIG. 1, the rotating unit 130 includes a specimen holding cylinder 132, which functions as the point of connection with the coupler 120. The specimen holding cylinder 132 defines a blind bore 134 having an opening configured to receive a first end of a CNT specimen 180 therein. Depending on the specific implementation, the bore 134 can define a threaded socket to engage corresponding threads 310 provided on the first end of the CNT specimen 180. According to another implementation, however, the bore 134 can be specifically sized to receive the specimen 180. A first locking mechanism 136 can be used to securely retain the specimen 180 within the opening 134. The locking mechanism 136 can be configured in various ways. According to the illustrated embodiment, one or more first clamping bolts 138 can be used to perform the function of the locking mechanism 136. The first clamping bolts 138 can be inserted into the specimen holding cylinder 132 in order to contact the CNT specimen 180 and securely retain it within the specimen holding cylinder 132. A first bearing support 140 is securely mounted on the platform 194 for holding the specimen holding cylinder 132 at a particular height corresponding to and in alignment with the motor shaft 112 and the rotational axis 116. The first bearing support 140 includes an opening in which a holding bearing 142 is disposed. The specimen holding cylinder 132 is journaled into the holding bearing 142 in order to facilitate rotation thereof.

The loading unit 150 includes a specimen load cylinder 152 having a blind bore 154 configured to receive the second end of the specimen 180. Depending on the specific implementation, the blind bore 154 may define an internally threaded socket configured to securely retain the second end of the CNT specimen 180. More particularly, the threaded socket can be configured to match the external threading 320 on the outer surface of the CNT specimen 180 in order to engage in a secure manner. However, a second locking mechanism 156 can be provided to securely retain the second end of the specimen 180. For example, FIG. 1 illustrates one or more clamping bolts 158 that are inserted within the second specimen load cylinder 152 in order to contact and securely retain the CNT specimen 180.

Figure 2:
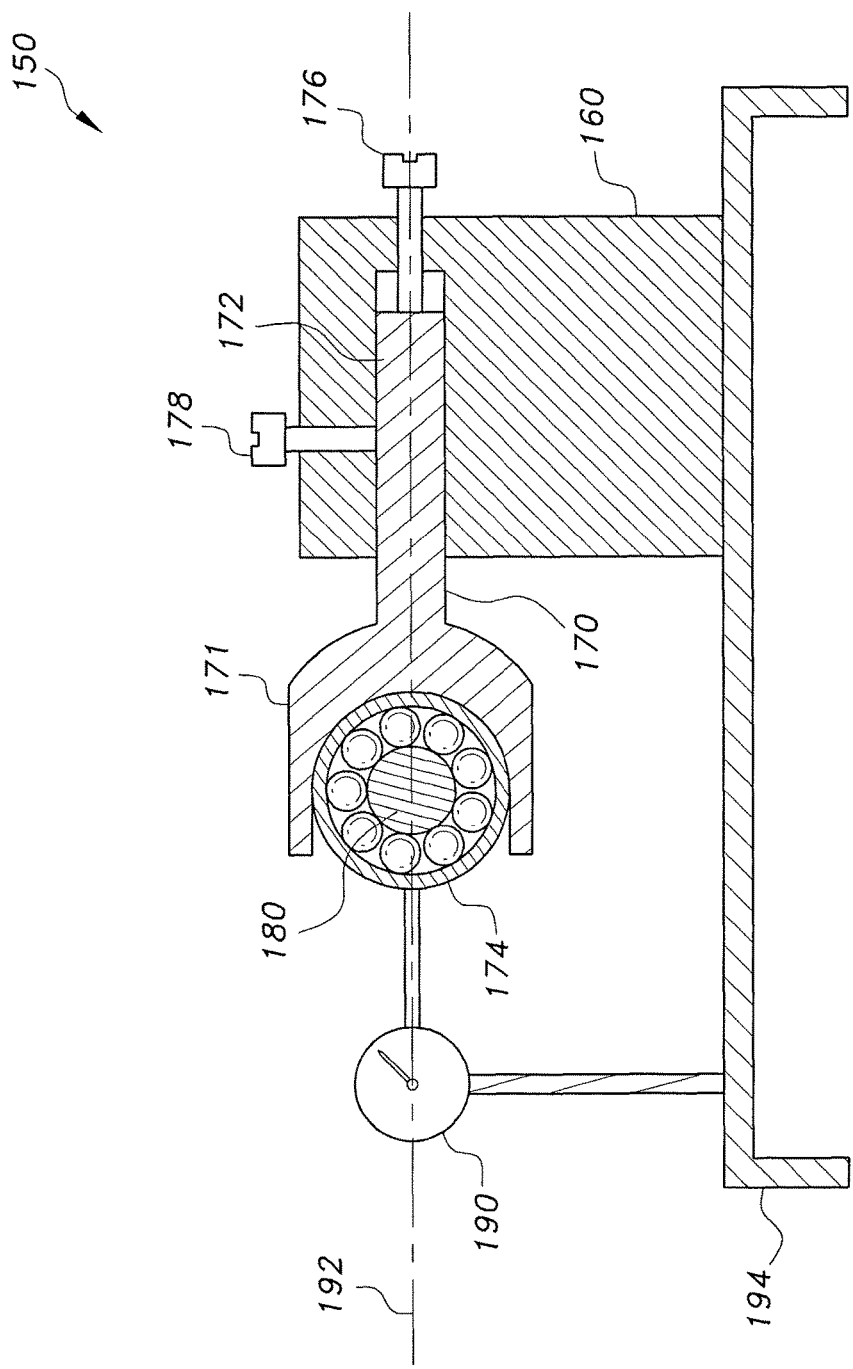
FIG. 2 is an environmental end view, partially in section, taken through the loading unit used in the fatigue cracking machine.

Referring additionally to FIG. 2, the loading unit 150 includes a load fork 170 that is used to apply a bending force to the CNT specimen 180. The bending force is applied along a bending axis 192 that is perpendicular to the rotational axis 116. Furthermore, the rotating unit 130 remains stationary relative to the rotational axis 116 while the bending force is applied. The loading fork 170 can be configured, for example, to include a first end 171 that is generally U-shaped and defined by a pair of tines, and a shaft 172 defining a second end. As illustrated in FIG. 2, the shaft 172 of the load fork 170 is disposed within a bearing support block 160, which is rigidly secured to the platform 194. A load bearing 174 is supported between the tines at the first end 171 of the loading fork 170. The load cylinder 152 is journaled into the load bearing 174 for rotation therewith. A load adjustment bolt 176 can be utilized to adjust the bending force exerted by the loading fork 170. The loading bolt 176 is threadable into the bearing support block 160 and bears against the end of the shaft 172 of the load fork 170. The adjustment bolt 176 can subsequently be adjusted in and out of the block in small increments to increase the amount of bending force exerted by displacement of the load fork 170.

Once an appropriate bending force has been achieved, a third clamping bolt 178 can be inserted into the bearing support block 160 in order to bear against the side of the shaft 172 to securely retain the load fork 170 in position. As further illustrated and FIG. 2, a dial indicator 190 is securely mounted on a post rigidly attached to the platform 194 that supports the other components of the machine. The dial indicator 190 has a plunger that bears against the load bearing 174 to measure the displacement of the load bearing 174 when the adjustment bolt 176 is used to alter the bending force, and also to show displacement of the load bearing 174 when the pre-crack is initiated and its extent as the crack propagates. Instead of a dial indicator 190 with an analog dial, an electronic digital indicator may be used to display the displacement.

In use, the CNT specimen 180 is mounted within the fatigue cracking machine 100 such that the circumferential notch 185 is precisely aligned with the opening to the bore 134 defined in the specimen holding cylinder 132. The bending force applied by displacement of the load bearing 174 is applied through the moment arm of the length of the specimen to form a crack at the notch 185 defined in the CNT specimen 180. Such embodiments differ from previous configurations wherein the circumferential notch 185 is located at a midpoint between the first and second bearing housings.

Once the CNT specimen 180 has been securely mounted within the specimen holding cylinder 132 and the specimen load cylinder 152, the loading bolt 176 is adjusted in order to generate the desired bending force on the CNT specimen 180. The third locking bolt 178 is then secured in order to maintain a constant bending force. The motor 110 is subsequently controlled in order to rotate the specimen 180 at a fixed or variable speed. The motor 110 can also be controlled to operate for a predetermined time period. For example, the motor can be controlled to operate at a constant velocity for a fixed time interval. Alternatively, the motor may be controlled to operate at a first velocity for a first time interval, a second velocity for a second time interval, a third velocity for a third time interval, etc.

Figure 3B:
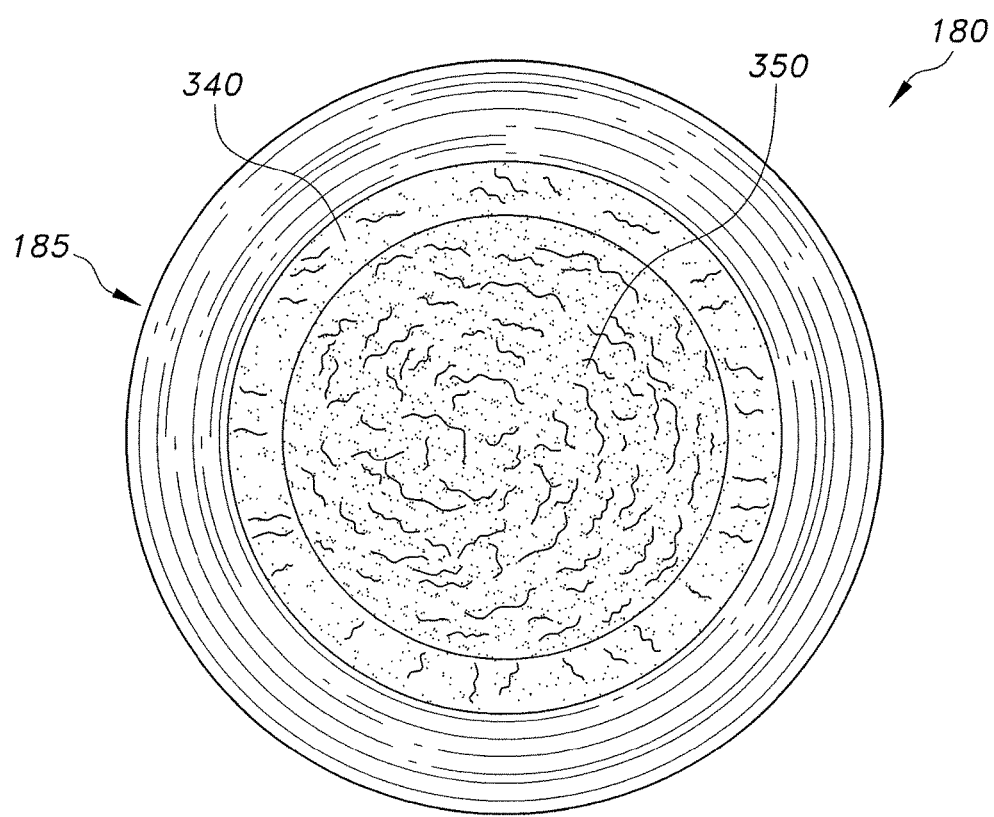
FIG. 3B is a section view through the notch of the CNT specimen of FIG. 3A, showing a fatigue crack produced by the machine of FIG. 1.
Figure 4A:
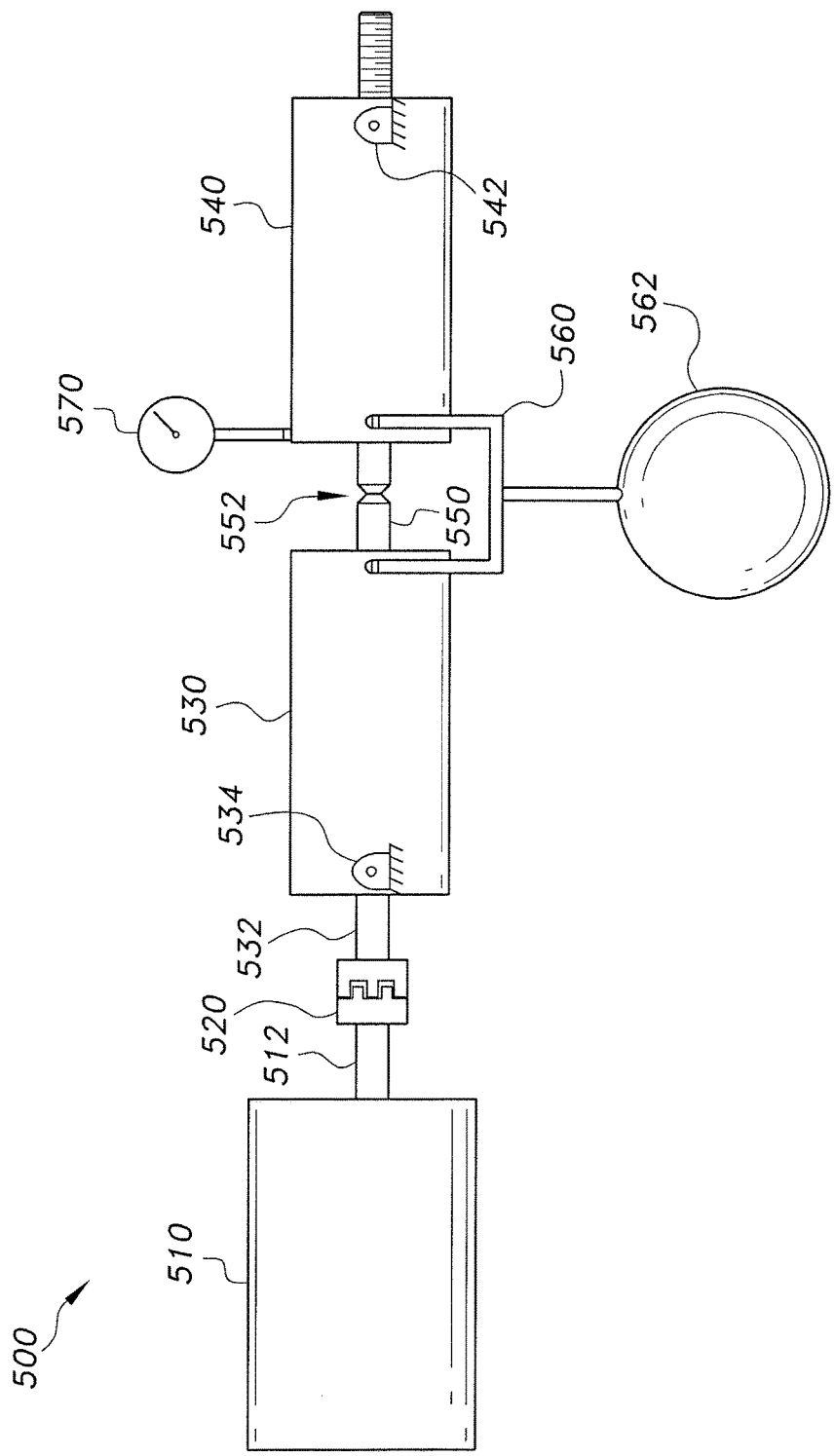
FIG. 4A is a diagrammatic side view of a conventional fatigue cracking device of the prior art using dead weight to apply a bending force to the specimen.
Figure 4B:
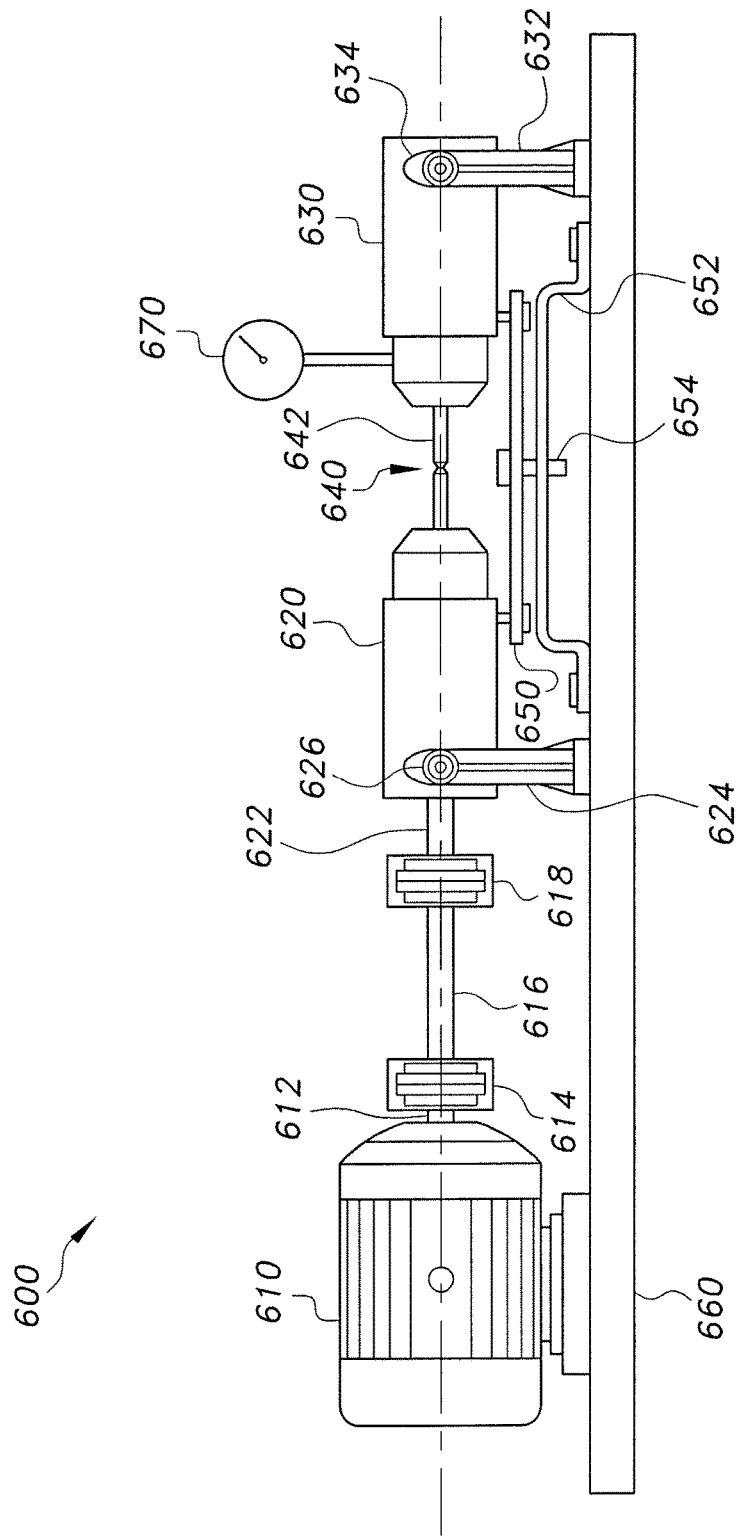
FIG. 4B is a diagrammatic side view of another conventional fatigue cracking device using pressure plates to apply a bending force to the specimen.
Figure 4C:
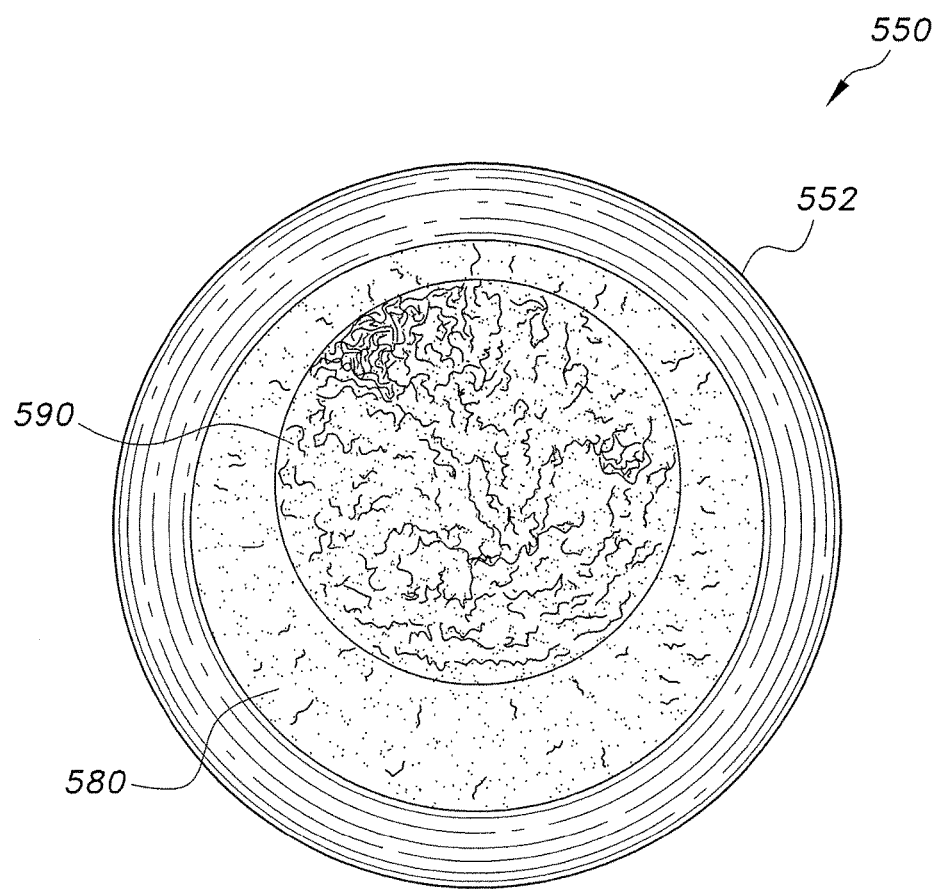
FIG. 4C is a section view through the notch of an exemplary CNT specimen subjected to fatigue cracking using the devices shown in FIGS. 4A and 4B, showing an eccentric cracking pattern.

As the CNT specimen 180 is rotated, the bending force will cause a fatigue crack to initiate at the circumferential notch 185 and propagate toward the center of the specimen 180. As the fatigue crack propagates, the displacement at the load bearing 174 will increase. FIG. 3B shows a section view through the notch 185 of an exemplary CNT specimen 180 subjected to pre-cracking in the present machine 100 of FIG. 1. The fatigue crack 340 and ligaments 350 are more nearly centered axially, compared to the section view of FIG. 4C.

It is to be understood that the fatigue cracking machine for circumferential notched tensile specimens is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A fatigue cracking machine for circumferential notched tensile (CNT) specimens, comprising:
   a platform;
   a motor securely mounted on the platform, the motor including a motor shaft;
   a bearing support securely mounted on the platform;
   a holding bearing mounted in the bearing support;
   an elongate holding cylinder defining a blind bore, the holding cylinder having a first end coupled to the motor shaft and a second end journaled into the holding bearing, the blind bore having an opening in the second end of the holding cylinder configured for receiving a first end of a CNT specimen into the blind bore;
   a bearing support block securely mounted on the platform;
   a load fork having a pair of tines defining a first end of the load fork and a shaft extending from the tines, the shaft having an end defining the second end of the load fork, the shaft being slidable within the bearing support block;
   a load bearing mounted between the tines of the load fork;
   an elongate load cylinder defining a blind bore, the load cylinder having a first end journaled into the load bearing for rotation therewith in alignment with the holding cylinder, the load cylinder having a second end, the blind bore having an opening defined in the second end of the load cylinder configured for receiving a second end of the CNT specimen into the blind bore;
   an adjustment bolt threadable in and out of the bearing support block to bear against the end of the shaft, the adjustment bolt adjusting displacement of the load fork;
   a support post rigidly mounted on the platform; and
   an indicator mounted on the support post, the indicator having a plunger bearing against the load bearing, the indicator being configured to measure displacement of the load bearing;
   wherein the machine forms a crack in the CNT specimen through a plane extending through the circumferential notch when the specimen is supported by the holding cylinder and the load cylinder with the circumferential notch aligned with the second end of the holding cylinder and the motor is activated to rotate the motor shaft and the adjustment bolt is threaded into the bearing support block to displace the load fork to apply a bending force to the CNT specimen, the displacement being measured by the indicator to monitor initiation and propagation of the crack.

2. The fatigue cracking machine according to claim 1, wherein the indicator comprises a dial indicator.

3. The fatigue cracking machine according to claim 1, wherein the indicator comprises an electronic digital indicator.

4. The fatigue cracking machine according to claim 1, further comprising a clamping bolt threadable into said bearing support block to bear against a side of the shaft of said load fork to clamp the load fork at a desired displacement.

5. The fatigue cracking machine according to claim 1, further comprising a first pair of clamping bolts threadable into said holding cylinder and a second pair of clamping bolts threadable into said load cylinder to secure the CNT specimen in said holding cylinder and said load cylinder, respectively.

6. The fatigue cracking machine according to claim 1, further comprising a coupler disposed between said motor shaft and said holding cylinder.

* * * * *